United States Patent [19]

Suzuki et al.

[11] Patent Number: 5,156,962
[45] Date of Patent: Oct. 20, 1992

[54] PROCESS FOR PRODUCING CARBOXYLIC ACID ESTERS USING CARBOXYESTERASE AND AN ANHYDRIDE IN ORGANIC SOLVENT

[75] Inventors: Takashi Suzuki, Takatsuki; Kazuhiko Ohta, Ikeda; Fumio Kikumoto, Yamatokoriyama, all of Japan

[73] Assignee: Takeda Chemical Industries, Ltd., Osaka, Japan

[21] Appl. No.: 526,761

[22] Filed: May 22, 1990

Related U.S. Application Data

[63] Continuation of Ser. No. 122,232, Nov. 13, 1987, abandoned.

[30] Foreign Application Priority Data

Nov. 28, 1986 [JP] Japan .................................. 61-28596

[51] Int. Cl.$^5$ .......................... C12P 7/02; C12P 19/62; C12P 19/00
[52] U.S. Cl. .................................. 435/135; 435/71.3; 435/76; 435/133; 435/280
[58] Field of Search .................. 435/135, 133, 280, 76, 435/71.3

[56] References Cited

U.S. PATENT DOCUMENTS

| 3,676,300 | 7/1972 | Yamamoto et al. | 195/29 |
| 3,691,181 | 9/1972 | Kishi et al. | 546/256 |
| 4,480,033 | 10/1984 | Suzuki et al. | 435/124 |
| 4,933,290 | 6/1990 | Cesti et al. | 435/280 |
| 4,996,158 | 2/1991 | Oda et al. | 435/280 |

FOREIGN PATENT DOCUMENTS 0149520 7/1985 European Pat. Off. .

OTHER PUBLICATIONS

Chem. Pharm. Bull., 28, 181 (1980).
J. Antibiotics, 27, 425 (1974).
J. Antibiotics, 28, 15 (1975).

*Primary Examiner*—David M. Naff
*Assistant Examiner*—Sandra Sancier
*Attorney, Agent, or Firm*—Wenderoth, Lind & Ponack

[57] ABSTRACT

A process for producing a carboxylic acid ester which comprises reacting a hydroxy compound for example a primary or secondary alcohol, lankacidin C or maridomycin with a carboxylic anhydride in the presence of carboxylesterase as a catalyst in an organic solvent.

19 Claims, No Drawings

PROCESS FOR PRODUCING CARBOXYLIC ACID ESTERS USING CARBOXYESTERASE AND AN ANHYDRIDE IN ORGANIC SOLVENT

This application is a continuation of now abandoned application Ser. No. 07/122,232 filed on Nov. 13, 1987.

BACKGROUND AND PRIOR ART

The present invention relates to a new process by enzymic reaction for producing a carboxylic acid ester. More particularly, the present invention relates to a process for producing a carboxylic acid ester which comprises reacting a hydroxy compound with a carboxylic anhydride in the presence of carboxyl esterase as a catalyst in an organic solvent.

Hitherto, synthetic reactions using organic chemical procedures and enzymic reactions have been used for producing a carboxylic acid ester.

As the synthetic reactions using organic chemical procedures, for example, esterification, such as the dehydration reaction of the following equation:

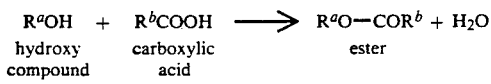

hydroxy compound | carboxylic acid | ester wherein a hydroxy compound is an acyl group acceptor and a carboxylic acid is an acyl group donor, and transesterification of the following equation:

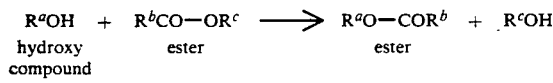

hydroxy compound | ester | ester wherein a hydroxy compound is an acyl group acceptor and an ester compound is an acyl group donor have been known.

As for the enzymic reaction, esterification, i.e. reverse hydrolysis where a hydroxy compound and a carboxylic acid are used as a substrate, and transesterification where a hydroxy compound and an ester compound are used as a substrate have been known.

However, when the hydroxy compound contains two or more hydroxy groups, one or more of the hydroxy groups can not selectively and specifically be converted into acyloxy group(s) by the synthetic reaction using organic chemical procedures.

For example, in the case that lankacidin A, i.e. a compound of the formula:

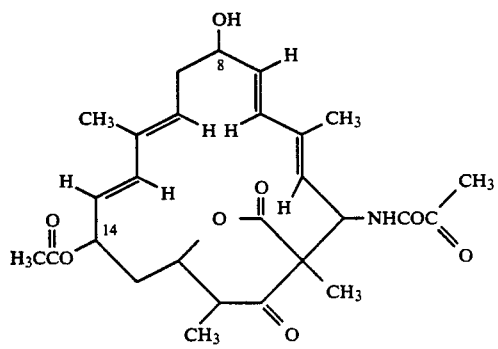

[This compound is effective as an antibacterial agent and antibiotic, e.g. antibiotic against swine dysentery infections (c.f. U.S. Pat. No. 3,676,300; and U.S. Pat. No. 4,480,033)] is produced from lankacidin C, i.e. a compound of the formula:

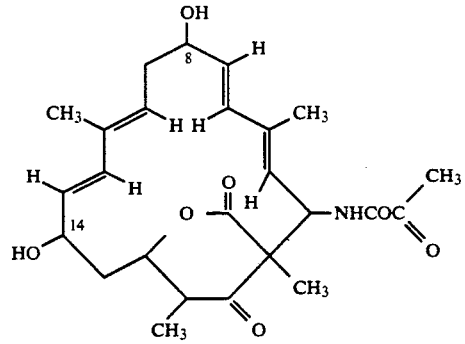

which has two hydroxy substituents at the 8- and 14-positions, a hydroxy group at the 14-position can not selectively and specifically be converted into an acyloxy group by the synthetic reaction.

Accordingly, for the purpose of converting hydroxy group(s) selectively and specifically into acyloxy group(s), the synthetic reaction using organic chemical procedures is not effective.

The enzymic reaction using a hydroxy compound and a carboxylic acid or ester compound as the substrate makes it possible to convert hydroxy group(s) selectively and specifically into acyloxy group(s) (c.f. U.S. Pat. No. 3,676,300 and U.S. Pat. No. 4,480,033).

However, in these enzymic reactions, a large amount of the substrate, such as a carboxylic acid or an ester compound is necessary, because the enzymes catalyze the chemical reaction in both forward and backward directions mainly depending upon the concentrations of substrates involved. Besides, the yield of the objective ester compound is very low.

Furthermore, in the esterification by enzymic reaction using a hydroxy compound and a carboxylic acid, the reaction must be conducted under completely anhydrous conditions. In the transesterification by enzymic reaction using a hydroxy compound and an ester compound, an ester compound as an acyl group donor often undergoes hydrolysis by carboxyl esterase catalyst, and hydolysis of the formed ester compound proceeds by carboxyl esterase at the same time. This makes it necessary to use a large excess of an ester compound (the substrate) as acyl group donor.

Besides, it is difficult to completely convert hydroxy group(s) into acyloxy group(s), because the transesterification by enzymic reaction is reversible by nature.

The present inventors studied the enzymic reaction to selectively and specifically convert hydroxy group(s) into acyloxy group(s) in high yield from a small amount of an acyl group donor.

As a result, the present inventors have found that in the enzymic reaction, the yield as well as quality of the objective ester compounds can remarkably be improved by employing a carboxylic anhydride as an acyl group donor in an organic solvent.

These findings were followed by continued studies, which have culminated in the present invention.

BRIEF SUMMARY OF THE INVENTION

The present invention provides a new process producing a carboxylic acid ester which comprises reacting a hydroxy compound with a carboxylic anhydride in the presence of carboxyl esterase as a catalyst in an organic solvent.

According to the process of the present invention, a carboxylic acid ester can be obtained easily, in high quality as well as high yield.

The process of the present invention is a novel esterase reaction which has not been known until now. By the process of the present invention, the hydroxy group(s) can selectively and specifically be converted into acyloxy group(s) and the ester compound can be obtained in high yield from a small amount of acyl group donor, because the esterase reaction of the present invention is an almost completely irreversible reaction. Thus the process of the present invention is industrially of great advantage.

DETAILED DESCRIPTION

As the carboxyl esterase of the present invention, use may be made of carboxyl esterase defined in Enzyme Nomenclature, IUB, 3-1-1-1, Academic press Inc, 1984. The carboxyl esterase of the present invention may originate in bacteria inclusive of Actinomyces, microorganisms e.g. Eumycetes and life, e.g. animals or plants.

The examples of the carboxyl esterase include animal liver esterase, such as porcine liver esterase [Sigma Co., U.S.A. This esterase can be prepared by the method described in Methods in Enzymology, 1, 657 (1955)] and T-2636 esterase (c.f. The Jounal of Antibiotics, 24, 1 (1971)) which originates in *Streptomyces rochei* var. volubilis.

The carboxyl esterase may be used in natural or purified form. Every extent of the purification of the carboxyl esterase is available in the present invention. For example, crude enzyme systems obtained by extracting proteins from culture broth or the purified single protein preparations may be employed.

Furthermore, for the reaction to proceed smoothly, organic solvent-soluble carboxyl esterase which is chemically modified may be employed in the present invention.

Referring to the method of modifying carboxyl esterase chemically, for example, 2,4-bis(o-methoxypolyethylene glycol)-6-chloro-s-triazine (hereinafter referred to briefly as activated $PEG_2$) may be brought into contact with enzyme proteins to obtain modified proteins which are coupled with polyethylene glycol [c.f. Biochemical and Biophysical Reseach Communications, 122(2) 845 (1984)].

In the present invention both of organic solvent-soluble or insolube carboxyl esterase can be used. Among these, preferred is organic solvent-soluble carboxyl esterase.

The carboxyl esterase may usually be used in the form of a solution thereof in an aqueous solvent (e.g. buffer solution such as tris-(hydroxymethyl)aminomethane-maleic acid buffer).

In case of organic solvent-soluble carboxyl esterase, the carboxyl esterase may be used in the form of a solution thereof in an organic solvent containing a small amount of water.

The carboxyl esterase may be used in the form of the culture filtrate of a carboxyl esterase-producing microorganism as such.

Furthermore, the carboxyl esterase may be used as an immobilized enzyme. In this case, the reaction is desirably conducted under conditions that the water phase is almost not formed. For example, the reaction may be conducted in such a manner that organic solvent-soluble carboxyl esterase is used as a column of immobilized enzyme and elution is conducted with an organic solvent containing a hydroxy compound as well as a carboxylic anhydride.

As the carboxylic anhydride of the present invention, use may be made of a carboxylic anhydride which is conventionally used in the field of an organic synthesis, such as peptide or antibiotic synthesis, which has the molecular weight below 350, preferably below 230 and which can dissolve in the organic solvent.

The examples of the carboxylic anhydride of the present invention include an anhydride formed by intermolecular condensation of 2 moles of the structurally same carboxylic acid to lose 1 mole of water, such as acetic anhydride, propionic anhydride, n-butyric anhydride, isobutyric anhydride, n-pentanoic anhydride, n-caproic anhydride or benzoic anhydride; and a mixed anhydride formed by intermolecular condensation of 2 moles of the structurally different carboxylic acid to lose 1 mole of water, such as a mixed anhydride of acetic acid and propionic acid, or a mixed anhydride of propionic acid and butyric acid. Among these, preferred is a carboxylic anhydride formed by intermolecular condensation of 2 moles of the structurally same carboxylic acid.

In the present invention, a carboxylic anhydride is used as an acyl group donor. For example, acyl groups to be donated are an acyl group which is derived from a monocarboxylic acid, such as acetyl or propionyl; an acyl group which is derived from an unsaturated aliphatic carboxylic acid, such as acryloyl or propioloyl; and an acyl group which is derived from a carbocyclic carboxylic acid, such as benzoyl or naphthoyl.

The carboxylic anhydride is preferably a compound of the formula:

wherein R and $R_1$ respectively is hydrogen, an alkyl, alkenyl, alkynyl, aryl or aralkyl.

Referring to the formula (I), the alkyl group is preferably a straight-chain or branched alkyl group of 1 to 10 carbon atoms, such as methyl, ethyl, n-propyl, isopropyl, n-butyl, tert-butyl, n-pentyl, n-hexyl, octyl, nonyl or decyl; or a 5 to 10 membered cycloalkyl group, such as cyclopentyl, cyclohexyl, cyclooctyl or cyclodecyl, and the alkenyl group is preferably a straight-chain or branched alkenyl group of 2 to 10 carbon atoms, such as vinyl, allyl, butadienyl, hexadienyl or decenyl; or a 5 to 10 membered cycloalkenyl group, such as cyclopentenyl, cyclohexenyl or cyclooctenyl, and the alkynyl group is prefeably a straight-chain or branched alkynyl group of 2 to 10 carbon atoms, such as ethynyl, propynyl, pentynyl or decynyl, and the aryl group is preferably an aryl group of 6 to 12 carbon atoms, such as phenyl, naphthyl or biphenylyl and the aralkyl group is preferably an aralkyl group of 7 to 10 carbon atoms, such as benzyl, phenethyl or phenacyl. Desirably R and $R_1$ are the same. Preferably R and $R_1$ an alkyl or aryl group.

More preferably, R and $R_1$ are a straight-chain or branched alkyl group of 1 to 5 carbon atoms, such as methyl, ethyl, n-propyl, iso-propyl, n-butyl, iso-butyl or n-pentyl; or phenyl.

A hydroxy compound used in the invention means an organic compound which contains one or more hydroxy groups attached to the constituent carbon atoms.

As the hydroxy compound, use is made of an organic compound containing 1 to 10, preferably 1 to 5 hydroxy groups which has the molecular weight below 1,500, preferably below 900, and which can dissolve in the organic solvent.

The specific examples of the hydroxy compound include alcohols, such as monovalent alcohols, e.g. methanol, ethanol, n-propanol, isopropanol or n-butanol, divalent alcohols, e.g. ethylene glycol or 1,4-butanediol, or polyvalent alcohols, e.g. glycerin; phenols, such as phenol, cresol, benzenetriol or hydroquinone; heterocyclic compounds, such as 8-quinolinol or hydroxypiperidine; antibiotics, such as tetracycline, leucomycin $A_1$, lankacidin C, chloramphenicol, cephalosporin, maridomycin or erythromycin; and biologically active substances, such as fibrostatin E or F.

Preferably the hydroxy compound is alcohols or antibiotics, more preferably lower ($C_{2-4}$) alcohols, lankacidin C or maridomycin.

Desirably the hydroxy compound is a compound of the formula:

$$R_2OH \qquad (II)$$

wherein $R_2$ is an organic residue.

Referring to the formula (II), the organic residue is an organic residue of the molecular weight below 1,000, such as an alkyl, alkenyl, alkynyl, aryl, aralkyl or heterocyclic group which may be substituted by suitable substituent(s).

Referring to the formula (II), the alkyl group is preferably a straight-chain or branched alkyl group of 1 to 30 carbon atoms, such as methyl, ethyl, n-propyl, isopropyl, n-butyl, tert-butyl, n-pentyl, n-hexyl, octyl, nonyl, dodecyl, undecyl or heneicosanyl; or a 5 to 20 membered cycloalkyl group, such as cyclopentyl, cyclohexyl, cyclooctyl, cyclodecyl or adamantyl and the alkenyl group is preferably a straight-chain or branched alkenyl group of 2 to 30 carbon atoms, such as vinyl, allyl, butadienyl, hexadienyl or undecenyl; or a 5 to 20 membered cycloalkenyl group, such as cyclopentenyl, cyclohexenyl or cyclooctenyl, and the alkynyl group is preferably a straight-chain or branched alkynyl group of 2 to 30 carbon atoms, such as ethynyl, propynyl, pentynyl, decynyl or undecynyl, and the aryl group is preferably an aryl group of 6 to 14 carbon atoms, such as phenyl, naphthyl, anthranyl or biphenylyl and the aralkyl group is preferably an aralkyl group of 7 to 19 carbon atoms, such as benzyl, phenethyl, phenacyl or trityl, and the heterocyclic group is preferably a 5 to 20 membered heterocyclic group containing 1 to 5 nitrogen atoms, 1 to 5 sulfur atoms or/and 1 to 5 oxygen atoms which may be condensed with a 5 to 8 membered alicyclic ring, such as cyclopentane or cyclooctane ring, an aromatic ring of 6 to 14 carbon atoms, such as benzene or anthracene ring, or 4 to 8 membered heterocyclic ring, such as azetidine or thiacyclohexane ring.

The examples of the substituent(s) on the said alkyl, alkenyl, alkynyl, aryl or aralkyl group include hydroxy, alkoxy (e.g. methoxy, ethoxy, propoxy or t-butoxy), nitro, optionally substituted amino (e.g. acylated amino or protected amino), optionally substituted sulfo (e.g. methylthio, ethylthio or iso-propylthio) and heterocyclic group (e.g. pyridyl, thienyl, benzothienyl or quinolyl).

The examples of the substituent(s) on the heterocyclic group include alkyl, alkenyl, alkynyl, aryl, aralkyl, hydroxy, alkoxy (e.g. methoxy, ethoxy, n-propoxy or t-butoxy), nitro, optionally substituted amino (e.g. acylated amino or protected amino) and optionally substituted sulfo (e.g. methylthio, ethylthio or n-propylthio). The alkyl, alkenyl, alkynyl, aryl or aralkyl group are as defined hereinbefore referring to the formula (II).

When lankacidin C is used as a hydroxy compound, it is feasible to employ a solution of lankacidin C in an organic solvent as well as the filtrate of culture broth as will be described in Example 5.

The carboxylic anhydride is used in an amount of about 1 to 100 equivalent weight moles, preferably 2 to 20 equivalent weight moles per the hydroxy compound.

As the organic solvent in the present invention, use may be made of an organic solvent which is pH about 3 to 10 and which will not inactivate carboxyl esterase under the reaction conditions.

The examples of the organic solvent include chain hydrocarbons, e.g. n-hexane, n-heptane, n-pentane, isohexane, methylene dichloride, chloroform, carbon tetrachloride, ethylene chloride, ethylidene chloride, vinylidene chloride, butyl chloride, amyl chloride, allyl chloride, ethyl bromide, ethylene bomide, chloroethyl bromide or fluorotrichloromethane; cylclic hydrocarbons, e.g. cyclohexane, methylcyclohexane, decahydronaphthalene, benzene, toluene, xylene, ethylbenzene, 1,2,3,4-tetrahydronaphthalene, chlorobenzene, o-dichlorobenzene, bromobenzene, o-chlorotoluene, or α-chloronaphtalene; ethers, e.g. ethyl ether, dichloroethyl ether or ethylene glycol monomethyl ether; acetals, e.g. methylal or acetaldehyde diethyl acetal; heterocyclic compounds, e.g. furan, furfural, 2-methylfuran, tetrahydropyran, 1,2-propylene oxide, epichlorohydrin, 1,4-dioxane, pyridine, morpholine; ketones, e.g. methyl ethyl ketone, methyl n-propyl ketone, methyl n-butyl ketone, methyl isobutyl ketone, methyl n-amyl ketone, diethyl ketone, ethyl n-butyl ketone, diacetone alcohol, mesityl oxide, cyclohexanone, methylcyclohexanone, acetophenone or acetonylacetone; esters, e.g. methyl formate, ethyl formate, methyl acetate, ethyl acetate, methyl propionate, methyl butyrate, ethyl acetacetate, methyl benzoate, methyl salicylate, ethyl abietate, diethyl oxalate, diethyl malonate, diethyl phthalate or dioctyl adipate; phosphates, e.g. triethyl phosphate; carbonates, e.g. diethyl carbonate; amines, e.g. trimethylamine; amides, e.g. formamide, N,N-dimethylformamide; nitriles, e.g. acetonitrile; sulfur-containing compounds, e.g. carbon disulfide or dimethylsulfoxide; and petroleum distillates, e.g. petroleum ether, petroleum benzine or ligroin.

Preferred is an organic solvent which can form two-phase with water.

Among these, ketones and esters are preferred. Especially methyl ethyl ketone, methyl n-propyl ketone, methyl n-butyl ketone, methyl isobutyl ketone, methyl acetate and ethyl acetate are preferred.

The above mentioned carboxylic anhydride or hydroxy compound also can serve as an organic solvent of the present invention.

The reaction of the present invention may preferably be conducted by adding carboxyl esterase to a mixture of carboxylic anhydride and a hydroxy compound in an organic solvent and stirring the mixture well.

In the case that a large amount of water is involved in the reaction, i.e. where carboxyl esterase insoluble in an organic solvent is usually employed, the reaction may preferably be conducted in one-phase system by stirring well until a water-in-oil emulsion is formed.

In the case that a very small amount of water is involved in the reaction, i.e. where carboxyl esterase soluble in an organic solvent is usually employed, the reaction may be conducted by stirring well until a homogeneous solution is formed.

The reaction temperature and pH value should vary with different types of cultures enzymes, substrates or solvents, and it is usually desirable to conduct the reaction at a temperature of about 5° to 90° C., preferably about 20° to 70° C. and at a pH between about 2 to 10, preferably about 3 to 9.

The thus obtained ester compound can be isolated and purified by conventional procedures, such as filtration, distillation, concentration, concentration under reduced pressure, chromatography e.g. chromatography employing silica gel or alumina, crystallization or recrystallization.

The following Examples and Reference Examples are given to illustrate the present invention, but they should not be construed to limit the scope of the present invention.

In the following Examples and Reference Examples, all % are % by weight per volume, unless otherwise specified.

REFERENCE EXAMPLE 1

Preparation of enzyme 500 ml of a culture medium containing glucose (3.0%), Proflo(Traders Oil Mill Co., U.S.A.) (1.0%), corn steep liquor (3.5%), magnesium sulfate (0.02%), dipotassium hydrogen phosphate (0.1%), soybean oil (0.05%) and calcium carbonate (1.5%) was controlled to pH 7.0 with a 20% aqueous sodium hydroxide solution.

The culture medium was put in a 2 liter Sakaguchi-flask and sterilized after plugged with cotton. The culture medium was then inoculated with a slant culture of *Streptomyces rochei* var. volubilis (IFO 12507) (ATCC-21250) (c.f. Japanese laid-open patent publication No.183695/1984) and incubated on a reciprocal shaker (83 spm) at 28° C. for 24 hours.

30 liters of a culture medium of the same composition as above was placed in a 50 liter fermentor and sterilized. 500 ml of the above mentioned culture broth was inoculated into the above culture medium and incubated at 24° C. for 24 hours with aeration of 1 VVM (aeration volume per minute per volume of the medium) and stirring at 150 rpm.

This was used as a seed culture. In a 200 liter fermentor, was placed 100 liters of a culture medium containing glycerol (10%), Proflo(Traders Oil Mill Co., U.S.A.) (2.0%), corn steep liquor (0.5%), Polypepton(-Daigo Nutritive Chemicals Ltd., Japan) (1.0%), ferrous sulfate (0.1%), soybean oil (0.01%) and β-cyclodextrin (2.0%), followed by adding a 20% aqueous sodium hydroxide solution to adjust the cultrure medium to pH 7.0, and then it was sterilized by steam at 120° C. for 20 minutes.

To this culture medium, 5 liters of the above mentioned seed culture was transplanted and incubated at 24° C. for 96 hours with the aeration of 1 VVM and stirring at 165 rpm. To 60 liters of the culture both thus obtained, were added 20 liters of water and 2 kg of Hyflo-Supercel (Johns Manville Products Co., U.S.A.) and the mixture was filtered to give 70 liters of the filtrate.

In a 60 liter vessel, 10 liters of the filtrate were placed, followed by adding 40 liters of ethanol, and the mixture was stirred well with a stirring rod. The mixture was allowed to stand at 5° C. for 12 hours so that proteins precipitated. The supernatant liquid was removed by siphon to obtain white-turbid precipitates.

The precipitates were centrifugated at 2000×g, keeping the temperature at 5° C. to reduce the water content of the precipitates as much as possible. The obtained product was washed with ethanol, and again centrifugated by the same procedure as above. The precipitates were collected and dried under reduced pressure of 50 mmHg at 10° C. for 24 hours to obtain about 200 g of powders. The powders are dissolved in 500 ml of 0.05M tris(hydroxymethyl)aminomethane-hydrochloric acid buffer (pH 7.4) and the insoluble matter was removed by centrifugation at 2000×g keeping the temperature at 5° C. to obtain the solution containing proteins.

To the thus obtained solution, 2 liters of ethanol was added and mixed well so that proteins precipitated again. The mixture was allowed to stand at 5° C. for 24 hours, and the supernatant liquid was removed by siphon. The precipitates were subjected to centrifugation of 2,000×g at 5° C. to remove supernatant liqiud completely, and washed with ethanol, and centrifugated by the same procedure as above, to collect the precipitates. The precipitates were dried under reduced pressure of 50 mmHg at 10° C. for 24 hours to obtain about 100 g of proteins as powders.

The powders were dissolved in 300 ml of 0.05M tris(-hydroxymethyl)aminomethane-hydrochloric acid buffer (pH 7.4) and insoluble matters were removed by centrifugation of 2,000×g at 50° C.

Thus obtained solution was subjected to gel filtration using a column (diameter: 200 mm, length: 1,500 mm) packed with Sephadex G-50 equilibrated with 0.05M tris(hydroxymethyl)aminomethane-hydrochloric acid buffer (pH 7.4). The column was eluted with the same buffer solution as above in flow rate of 20 ml per 5 min.

By a method for assaying activity of carboxyl esterase using p-nitrophenylacetic acid [c.f. Journal of Biological Chemistry 170, 467 (1947)], 400 ml of fractions showing activity of carboxyl esterase was collected, to which 2.4 liters of ethanol was added, and the resulting mixture was stirred with a stirrer in a 3 liter Erlenmeyer flask to give precipitates of proteins. The mixture was allowed to stand at 5° C. for 24 hours, and the precipitates were collected by centrifugation of 2,000×g at 5° C., followed by drying under reduced pressure of 50 mmHg at 10° C. for 24 hours to give 40 g of proteins as powders.

The powders were dissolved in 100 ml of 0.05M tris(-hydroxymethyl)aminomethane-hydrochloride buffer (pH 7.4). The solution was subjected to gel filtration using a column (diameter: 100 mm, length: 1,500 mm) packed with Sephadex G-100, the elution being conducted with the same buffer solution as above in flow rate of 10 ml per 5 min.

The fractions showing activity of carboxyl esterase were collected, and were subjected to linear gradient ion-exchange chromatography using increasing salt concentration by the use of a column (diameter: 50 mm, length: 400 mm) packed with DEAE Sephadex A-50. The elution was conducted with 2 liters of 0.05M tris(- hydroxymethyl)aminomethane-hydrochloric acid buffer (pH 7.4) containing 1 molar concentration of sodium chloride in the 1st vessel as well as 2 liters of 0.05M tris(hydroxymethyl)aminomethane-hydrochloric acid buffer (pH 7.4) in the 2nd vessel.

10 ml each of the eluate was fractionated by a fraction collector (Toyo 5F-160K type), and 300 ml of the fractions showing activity of carboxyl esterase was collected, and salted-out with 200 g of crystalline ammonium sulfate while stirring in a 1 liter Erlenmeyer flask.

The obtained products were allowed to stand at 5° C. for 24 hours so that the proteins completely precipitated, and the precipitates were collected by centrifugation of 2,000×g at 5° C. In 50 ml of 0.05M tris(hydroxymethyl)aminomethane-hydrochloric acid buffer (pH 7.4) were dissolved the obtained precipitates, and the solution was subjected to gel-filtration using Sephadex G-100 in the same manner as above.

The fractions showing activity of carboxyl esterase were collected and subjected to linear gradient ion-exchange chromatography using DEAE Sephadex A-50 in the same manner as above to collect 250 ml of the fractions showing activity of carboxyl esterase, followed by salting out by adding 167 g of ammonium sulfate while stirring.

After standing at 5° C. for 24 hours, the precipitates were separated by centrifugation in the same manner as above. The precipitates were dissolved in 30 ml of 0.05M tris(hydroxymethyl)aminomethane-hydrochloric acid buffer (pH 7.4) and subjected to gel filtration using Sephadex G-100 in the same manner as above. The obtained fractions showing activity of carboxyl esterase were chromatographed on a column (diameter: 10 mm, length: 100 mm) of DEAE Sephadex A-50 equilibrated with 0.05M tris(hydroxymethyl)aminomethane-hydrochloric acid buffer (pH 7.4), the elution being conducted by 100 ml of the same buffer solution as above and 20 ml of the same buffer solution as above containing 1 molar concetration of sodium chloride successively.

The fractions showing activity of carboxyl esterase were collected, injected into tube made of cellophane for dialysis and placed under 2 liters of water in a 3 liter Erlenmeyer flask to conduct dialysis. The dialysis was continued for 24 hours by stirring external water with a magnetic stirrer. After completion of dialysis, the solution in tube was put in a 2 liter eggplant type flask and lyophlized under reduced pressure fo 20 mmHg for 24 hours using a lyophilizer (No 10-146, MR-BA type, The Virtis Co. Inc., U.S.A.) to obtain powdery carboxyl esterase [c.f. Enzyme Nomenclature, Section 3.1.1.1, Academic Press Inc. (1984)] which originates in *Streptomyces rochei* var. volubilis. The obtained carboxyl esterase was confirmed to be single protein by SDS gel electrophoresis and ultracentrifugal analysis. Hereinafter, sometimes the above carboxyl esterase is referred to briefly as carboxyl esterase preparation.

REFERENCE EXAMPLE 2

Preparation of chemically modified enzyme

In 8 ml of 0.1M sodium borate buffer (pH 9,5) was dissolved 50 mg of carboxyl esterase preparation, to which was added 1.0 g of 2,4-bis(o-methoxypolyethylene gylcol)-6-chloro-s-triazine (molecular weight of polyethylene glycol: 6,000), followed by stirring at 5° C. for 1 hour. To the reaction mixture was added 72 ml of 0.2M potassium phosphate buffer (pH 7.0) to stop the reaction.

The reaction mixture was subjected to ultrafiltration (ultrafiltrator: 8050 type. Amicon Division of GRACE Corp., U.S.A.) with miliporfiter YM-10, and washed with 400 ml of 0.2M potassium phosphate buffer (pH 7.0) to remove unreacted 2,4-bis(o-methoxypolyethylene glycol)-6-chloro-s-triazine.

Then the solution containing enzyme modified with polyethylene glycol was put in a 500 ml eggplant type flask and lyophilized under pressure of 20 mmHg for 24 hours to obtain 600 mg of carboxyl esterase modified with polyethylene glycol (hereinafter referred to briefly as PEG-modified esterase).

EXAMPLE 1

2 ml of a solution of 11 mM concentrations of lankacidin C and 50 mM concentrations of acetic anhydride in methyl isobutyl ketone was put in a 20 ml test tube with stopper, to which was added 0.3 ml of a solution of PEG-modified esterase in 0.2M tris(hydroxymethyl) aminomethane-maleic acid buffer (pH 7.0), the concentration of PEG-modified esterase of which was 12 mg per ml, followed by shaking with shaking apparatus (80 spm) at 37° C.

By high-performance liquid chromatography (hereinafter referred to briefly as HPLC method) as described below, the amount of lankacidin A formed was measured at the time shown in Table 1.

The condition of HPLC method was as follows:

| Equipment: | LC-5A type (Shimazu Corporation, Japan) |
|---|---|
| Column: | μ Porasil column (300 × 3.9 mmφ, Waters Division of Millipore, U.S.A.) |
| Temperature: | 45° C. |
| Flow rate: | 1.2 ml per min. |
| The retention time of lankacidin C and lankacidin A was as follows: | |
| Lankacidin C: | 7.0 min. |
| Lankacidin A: | 3.5 min. |

The amount of lankacidin A was quantitatively determined by using an ultraviolet absorption detector for 254 nm.

As a control, using ethyl acetate (300 mM) or acetic acid (100 mM) instead of acetic anhydride (50 mM), the same procedures as above were conducted. The results were shown in Table 1.

TABLE 1

| | Amount (mM) of lankacidin A formed at time intervals | | |
|---|---|---|---|
| | Acetyl group donor | | |
| Reaction time (min.) | Acetic anhydride (50 mM) | Ethyl acetate (300 mM) | Acetic acid (100 mM) |
| 0 | — | — | — |
| 10 | 5.58 | 0.54 | — |
| 20 | 8.11 | 0.69 | — |
| 30 | 9.09 | 0.95 | — |
| 45 | 9.30 | 1.45 | — |
| 80 | 10.83 | 1.98 | — |
| 110 | 10.83 | 2.10 | — |

*— in Table means not more than 0.1 mM

Table 1 shows clearly that acetic anhydride is superior to ethyl acetate or acetic acid in the rate of formation and amount of lankacidin A formed and acetic acid can not be used practically.

EXAMPLE 2

By changing the concentration of acetyl group donor to those shown of Table 2, with the reaction time being 20 min., the same procedure as in Example 1 was conducted. The results were shown in Table 2.

TABLE 2

Amount (mM) of lankacidin A formed by different acetyl group donors

| Acetyl group donor | (mM) | Amount of lankacidin A formed (mM) |
|---|---|---|
| Acetic anhydride | 1 | 0.55 |
|  | 2 | 1.06 |
|  | 3 | 1.40 |
|  | 5 | 2.51 |
|  | 7 | 3.44 |
|  | 10 | 4.76 |
|  | 15 | 6.93 |
|  | 20 | 7.28 |
| Ethyl acetate | 500 | 0.85 |
|  | 1000 | 1.05 |
|  | 2000 | 1.76 |
|  | 3000 | 2.39 |
|  | 4000 | 3.28 |
|  | 5000 | 3.95 |
|  | 6000 | 4.33 |
|  | 7500 | 4.95 |
|  | 10000 | 6.13 |

By using Lineweaver-Burk's equation of the formula ② [Biochemical Dictionary, first edition, page 1314 (1984), Tokyokagakudozin Ltd.] derived by modifying the Michaelis-Menten equation of formula ① [Op Cit. page 1239], the reaction using acetic anhydride as an acetyl group donor was compared with that using ethyl acetate as acetyl group donor.

$$v = \frac{V\max \cdot [S]_o}{[S]_o + Km} \quad (1)$$

$$\frac{1}{v} = \frac{Km}{V\max} \cdot \frac{1}{[S]_o} + \frac{1}{V\max} \quad (2)$$

$v$: Reaction velocity
$V\max$: Maximal reaction velocity
$[S]_o$: Concentration of substrates
$Km$: Michaelis Constant By putting values of the concentration of acetyl group donor shown in Table 2 in the place of $[S]_o$, and values of the amount of lankacidin A formed shown in Table 2 in the place of $v$, values of $Km$ and $V\max$ were calculated by means of the least-squares method.

The results were shown in Table 3.

TABLE 3

| Acetyl group donor | Km (mM) | Vmax (mM/20 min.) |
|---|---|---|
| Acetic anhydride | 7.69 | 6.59 |
| Ethyl acetate | 3010 | 5.40 |

Table 3 shows clearly that in the case that acetic anhydride is used as an acetyl group donor, reaction products can sufficiently be obtained from a small amount of substrates, because the value of Km is much smaller than that in the case that ethyl acetate is used as an acetyl group donor.

EXAMPLE 3

To a 10 liter glass lined reactor equipped with a stirrer was added 2 liters of methyl isobutyl ketone which was kept at 37° C., in which was dissolved 10 g of lankacidin C. To the mixture, was added a solution of 1.2 g of PEG modified esterase in 300 ml of 0.2M tris(hydroxymethyl) aminomethane-maleic acid buffer (pH 7.0). After mixing, 10 ml of acetic anhydride was added to the mixture, followed by stirring at 37° C. for 40 min.

To the reaction mixture was added 2 liters of distilled water with stirring. After mixing, the reaction mixture was put in a 10 liter separatory funnel to remove water layer. To the obtained organic solution was added 500 ml of a 2% aqueous sodium bicarbonate solution and stirred well, followed by removing water layer.

The obtained mixture was again washed with the same aqueous sodium bicarbonate solution as above to remove an excess acid. Washing with 2 liters of distilled water was twice conducted in a separatory funnel to separate an organic layer.

The thus obtained organic solution was put in a 3 liter Erlenmeyer flask, dried over sodium sulfate for 2 hrs. and concentrated under reduced pressure to dryness to obtain 10 g of lankacidin A as crude crystals.

In 1 liter of chloroform were dissolved the above crystals, and the solution was absorbed in silica gel (Merck Co, U.S.A.) column ($\phi$: 80 mm, length: 500 mm) equilibrated with chloroform. After washing with 2 liters of chloroform, the elution was conducted with ethyl acetate:chloroform (3:7 v/v"). 20 ml each of fractions was taken in a fraction collector (Toyo fraction collector, 5F-160K type). The fractions containing lankacidin A were collected, using ultraviolet spectroscopy.

The obtained solution was concentrated under reduced pressure to dryness to give lankacidin A as powder.

To the powder was added 1 liter of ethyl acetate and the resultant solution was concentrated under reduced pressure to 40 ml, followed by cooling at 5° C. Crystals of lankacidin A which separated out were collected by glass filter, washed with n-hexane, and dried under pressure of 20 mmHg at 40° C. to obtain 8.1 g of lankacidin A as crystals.

Melting point, optical rotation, ultraviolet spectrum and elemental analysis of the obtained crystals were respectively confirmed to be identical with those of the compound described in the Journal of Antibiotics 24, 13 (1971).

Retention time of the obtained crystals in HPLC method was confirmed to be identical with that of an authentic sample of lankacidin A.

EXAMPLE 4

To a 10 liter glass lined reactor equipped with a stirrer was added 2 liters of methyl isobutyl ketone, in which 10 g of lankacidin C was dissolved at 37° C. To the solution was added 1 liter of a solution of carboxyl esterase preparation obtained in Reference Example 1 in 0.2M tris(hydroxymethyl)aminomethane-maleic acid buffer (pH 7.0), concentration of the carboxy esterase preparation of which was 2 mg per ml.

To the mixture was added 10 ml of acetic anhydride, followed by stirring at 37° C. for 40 min. To the reaction mixture was added 2 liters of distilled water, and stirred well and then put in a 10 liter separatory funnel.

According to the same procedure as in Example 3, 5.8 g of lankacidin A was obtained as crystals.

EXAMPLE 5

The filtrate of culture broth obtained by cultivating *Streptomyces rochei* var. volubilis in Reference Example 1 contains carboxyl esterase which originated in *Streptomyces rochei* var. volubilis.

It has already known that *Streptomyces rochei* var. volubilis is capable of accumulating lankacidin C in culture broth, that is, *Streptomyces rochei* var. volubilis is a microorganism which is capable of producing lankacidin C. [The Journal of Antibiotics 24, 1 (1971)].

The content of lankacidin C in the said filtrate of culture broth was measured by HPLC method described in Example 1. The said filtrate was confirmed to contain lankacidin C in a concentration of 3500 μg per ml.

In Example 5, the filtrate of culture broth obtained in Reference Example 1 was used as the starting material which contained carboxyl esterase as well as a hydroxy compound. To a 10 liter glass lined fermentator with a stirrer was added 1 liter of the said filtrate and the temperature of the mixture was kept at 37° C.

To the mixture were added 1 liter of methyl isobutyl ketone which was kept at 37° C., and 10 ml of acetic anhydride, followed by stirring 37° C. for 60 min. The reaction mixture was centrifuged at 2000×g keeping the temperature at 5° C. by using a low temperature-centrifugal separator (RD-2 IV type, Tomy Seiko Co. Ltd., Japan).

The obtained solution was put in a 10 liter separatory funnel to separate the upper solution and it was washed with 2 liters of distilled water.

According to the same procedure as in Example 3, 2.8 g of lankacidin A was obtained.

EXAMPLE 6

By using 10 ml of propionic anhydride in place of 10 ml of acetic anhydride in Example 3, the same procedure as in Example 3 was conducted. The products accumulated in the solvent layer of the reaction mixture were identified and assayed by HPLC method of Example 1 where lankacidin C-14-propionate prepared according to the synthetic method described in The Journal of Antibiotics 26, 647 (1973) was employed as authenic sample.

The solvent layer was found to contain lankacidin C-14-propionate (Retention time: 2.40 min.) in a concentration of 9.1 g per liter. By the same procedure as in Example 3, 7.2 g of lankacidin C-14-propionate was separated and purified.

Melting point, optical rotation, elemental analysis and molecular extinction were respectively confirmed to be identical with those of the compound described in the Journal of Antibiotics 26, 647 (1973).

EXAMPLE 7

By using butyric anhydride, isobutyric anhydride, caproic anhydride or benzoic anhydride in place of propionic anhydride in Example 6, the same procedure as in Example 6 was conducted. The reaction mixture was assayed by HPLC method of Example 1 and the separation and purification was conducted by the method described in Example 3.

| Carboxylic anyhdride | Product | Retention time (min.) | Crop (g) |
|---|---|---|---|
| butyric anhydride | lankacidin C-14-n-butyrate | 2.03 | 5.70 |
| isobutyric anhydride | lankacidin C-14-isobutyrate | 1.89 | 5.60 |
| caproic anhydride | lankacidin C-14-caproate | 4.06 | 3.10 |
| benzoic anhydride | lankacidin C-14-benzoate | 4.90 | 3.21 |

Melting point, optical rotation, elemental analysis and molecular coefficient of the obtained compounds were confirmed to be identical with those described in The Journal of Antibiotics 26, 647 (1973).

EXAMPLE 8

To a 10 liter glass lined reactor with a stirrer were added 2 liters of methyl isobutyl ketone containing 1M of ethanol, and the temperature of solution was kept at 37° C. To the solution was added 300 ml of a solution of PEG modified esterase obtained in Reference Example 2 in 0.2M tris(hydroxymethyl)aminomethane-maleic acid buffer (pH 7.0), the concentration of PEG modified esterase of which was 12 mg per ml, and to the mixture was added acetic anhydride in a concentration as shown in Table 4, followed by stirring at 37° C. for 20 min.

Methyl isobutyl ketone layer was separated, and subjected to Gas Chromatography Analysis (GC), on the conditions mentioned below.

The conditions of Gas Chromatography:

| | |
|---|---|
| Equipment | GC-9A type, Shimazu Corporation, Japan |
| Column | Porapak P(60~80 meshes, φ: 3 mm, length: 2 m, Waters Co., U.S.A.) |
| Detector | FID type (Shimazu Corporation, Japan) |
| Pressure of hydrogen | 0.5 kg/cm$^2$ |
| Flow rate of hydrogen | 35 ml/min. |
| Pressure of air | 0.5 kg/cm$^2$ |
| Flow rate of air | 480 ml/min. |
| Column temperature | 140° C. |
| Temperature of injector and detector | 150° C. |
| Amount of sample | 5 μl |

The retention time of each of the ingredients:

| | |
|---|---|
| Ethyl acetate (product) | 4.1 min. |
| Ethanol | 1.3 min. |
| Acetic acid | 2.6 min. |
| Methyl isobutyl ketone | 6.0 min. |

Each of the ingredients was assayed by using special grade chemical (Wako Pure Chem. Ltd., Japan) as authentic sample. The results were shown in Table 4.

TABLE 4

| Acetic anhydride initial concentration (mM) in solvent | Ethyl acetate resultant concentration (mM) in solvent | Acetic acid resultant concentration (mM) in solvent |
|---|---|---|
| 0 | 0 | 0 |
| 2.5 | 2.4 | 2.5 |
| 5.0 | 5.2 | 4.9 |

TABLE 4-continued

| Acetic anhydride initial concentration (mM) in solvent | Ethyl acetate resultant concentration (mM) in solvent | Acetic acid resultant concentration (mM) in solvent |
| --- | --- | --- |
| 10 | 9.8 | 8.2 |
| 15 | 15.2 | 12.3 |
| 20 | 19.3 | 18.3 |
| 30 | 24.0 | 23.8 |
| 40 | 25.1 | 24.5 |
| 50 | 26.2 | 25.1 |

EXAMPLE 9

In case of 30 mM concentration of acetic anhydride in Table 4 of Example 8, the formed ethyl acetate was separated according to the procedure described below.

To the reaction mixture, 5 liters of distilled water was added, stirred well and put in a 10 liter separatory funnel. After standing for 1 hour, water layer was removed. To the obtained organic layer was added 500 ml of a 2% aqueous sodium bicarbonate solution, and mixed well in a separatory funnel.

After standing for 1 hour, a water layer was removed, and to the obtained organic solution was added 5 liters of distilled water. According to the same procedure as above, the water layer was removed.

The obtained mixture was three times washed with the aqueous sodium bicarbonate solution according to the same procedure as above, to remove enzyme protein, ethanol and acetic acid in the reaction mixture. After additional washing with 5 liters of distilled water, the mixture was distilled at 77° C. and atmospheric pressure by batch fractional column to obtain ethyl acetate.

Specific gravity at 20° C., refractive index and boiling point of the obtained compound were confirmed to be identical with those described in Merck Index, the 8th edition (1968).

EXAMPLE 10

By using 2,4-bis(o-methoxypolyethylene glycol)-6-chloro-s-triazine, PEG modified esterase of carboxyl esterase (Enzyme Nomenclature, 3.1.1.1) (Sigma Co., U.S.A.) which originated in porcine liver was prepared according to the same procedure as in Reference Example 2.

By using the PEG modified esterase, acetic anhydride was allowed to react with ethanol according to the same procedure as in Example 8, and the resultant ethyl acetate and acetic acid were assayed following the same quantitative analysis method as in Example 8.

The results were shown in Table 5.

TABLE 5

| Acetic anhydride initial concentration (mM) in solvent | Ethyl acetate resultant concentration (mM) in solvent | Acetic acid resultant concentration (mM) in solvent |
| --- | --- | --- |
| 0 | 0 | 0 |
| 2.5 | 2.4 | 2.6 |
| 5.0 | 5.0 | 4.9 |
| 10 | 9.5 | 8.3 |
| 15 | 14.9 | 13.0 |
| 20 | 18.5 | 17.8 |
| 30 | 23.5 | 22.9 |
| 40 | 24.0 | 24.1 |
| 50 | 25.9 | 25.0 |

EXAMPLE 11

In the case that initial concentration of acetic anhydride was 30 mM in Table 5 of Example 10, the resultant ethyl acetate was separated by the same procedure as in Example 9 to give 3.05 g of ethyl acetate.

Specific gravity at 20° C., refractive index and boiling point were confirmed to be identical with those described in Merck Index, the 8th edition (1968).

EXAMPLE 12

To a 10 liter glass lined reactor with a stirrer was added 2 liters of methyl isobutyl ketone containing 1 molar concentration of ethanol, and the temperature of solution was kept at 37° C.

To the solution was added 300 ml of a solution of PEG modified esterase which originated in *Streptomyces rochei* var. volubilis prepared by the same procedure as in Reference Example 1, in 0.2M tris(hydroxymethyl)aminomethanemaleic acid buffer (pH 7.0), concentration of PEG modified esterase of which was 12 mg per ml.

After stirring at 37° C. for 10 min., 7.8 g of n-propionic anhydride was added to the mixture and stirred at 37° C. for 20 min. To the reaction mixture was added 5 liters of distilled water and stirred well and then put in a 10 liter separatory funnel. After standing for 1 hour, water layer was removed.

To the obtained organic layer was added 500 ml of a 2% aqueous sodium bicarbonate solution and mixed with shaking using a separatory funnel. After standing for 1 hour, a water layer was removed and to the obtained organic layer was added 5 liters of distilled water, and then the water layer was removed by the same procedure as above.

The obtained mixture was three times washed with an aqueous sodium bicarbonate solution according to the same procedure as above, to remove enzyme protein, ethanol and propionic acid in the reaction mixture.

The thus obtained mixture was distilled at 99° C. and atmospheric pressure by batch fractional column to obtain 5.5 g of ethyl propionate.

Specific gravity at 20° C., refractive index and boiling point of the obtained compound were confirmed to be identical with those described in Merck Index, the 8th Edition (1968).

EXAMPLE 13

By using 9.4 g of n-butyric anhydride in place of n-propionic anhydride, the same procedure as in Example 12 was conducted.

Distillation at 178° C. and atmospheric pressure by using batch fractional column gave 6.3 g of ethyl n-butyrate.

Specific gravity at 20° C., refractive index and boiling point of the obtained compound were confirmed to be identical with those described in Merck Index, the 8th Edition (1968).

EXAMPLE 14

By using 12.9 g of n-caproic anhydride in place of propionic anhydride, the same procedure as in Example 12 was conducted.

Distillation at 178° C. and atmospheric pressure by using batch fractional column gave 6.3 g of ethyl n-caproate.

Specific gravity at 20° C., refractive index and boiling point of the obtained compound were confirmed to be identical with those described in Merck Index, the 8th Edition (1968).

EXAMPLE 15

By using n-propanol in place of ethanol, the same procedure as in Example 12 was conducted.

Distillation at 124° C. and atmospheric pressure by using batch fractional column gave 6.0 g of n-propyl propionate.

Specific gravity at 20° C., refractive index and boiling point of the obtained compound were confirmed to be identical with those described in Merck Index, the 8th Edition (1968).

EXAMPLE 16

By using 9.4 g of n-butyric anhydride in place of propionic anhydride, and n-propanol in place of ethanol, the same procedure as in Example 12 was conducted.

Distillation at 143° C. and atmospheric pressure by using a batch fractional column gave 5.8 g of n-propyl n-butyrate.

Specific gravity at 20° C., refractive index and boiling point of the obtained compound were confirmed to be identical with those described in Merck Index, the 8th Edition (1968).

EXAMPLE 17

By using 6.1 g of acetic anhydride in place of propionic anhydride, and isopropanol in place of ethanol, the same procedure as in Example 12 was conducted.

Distillation at 89° C. and atmospheric pressure by using batch fractional column gave 5.0 g of isopropionyl acetate.

Specific gravity at 20° C., refractive index and boiling point of the obtained compound were confirmed to be identical with those described in Merck Index, the 8th Edition (1968).

EXAMPLE 18

By using 6.1 g of acetic anhydride in place of propionic anhydride, and n-butanol in place of ethanol, the same procedure as in Example 12 was conducted.

Distillation at 126° C. and atmospheric pressure by using batch fractional column gave 5.2 g of n-butyl acetate.

Specific gravity at 20° C., refractive index and boiling point of the obtained compound were confirmed to be identical with those described in Merck Index, the 8th Edition (1968).

EXAMPLE 19

By using n-butanol in place of ethanol, the same procedure as in Example 12 was conducted.

Distillation at 147° C. and atmospheric pressure by using batch fractional column gave 5.1 g of n-butyl propionate.

Specific gravity at 20° C., refractive index and boiling point of the obtained compound were confirmed to be identical with those described in Merck Index, the 8th Edition (1968).

EXAMPLE 20

By using 13.6 g of benzoic anhydride in place of propionic anhydride, the same procedure as in Example 12 was conducted.

Distillation at 212° C. and atmospheric pressure by using batch fractional column gave 9.2 g of ethyl benzoate.

Specific gravity at 20° C., refractive index and boiling point of the obtained compound were confirmed to be identical with those described in Merck Index, the 8th Edition (1968).

EXAMPLE 21

By using 12.2 g of acetic anhydride in place of propionic anhydride, and ethylene glycol in place of ethanol, the same procedure as in Example 12 was conducted.

Distillation at 182° C. and atmospheric pressure by using batch fractional column gave 2.0 g of 2-hydroxyethyl acetate.

Distillation at 191° C. and atmospheric pressure by using batch fractional column gave 2.2 g of 2-acetoxyethyl acetate.

Specific gravity at 20° C., refractive index and boiling point of the obtained compound were confirmed to be identical with those described in Merck Index, the 8th Edition (1968).

EXAMPLE 22

In a 200 liter fermentor, 100 liters of a culture medium containing dextrin (10%), Proflo (Traders Oil Mill Co., U.S.A.) (0.5%), defatted soy bean flour (2.0%), corn steep liquor (1.0%), corn gluten meal (1.3%), p-aminobenzoic acid (0.025%), ammonium sulfate (0.2%), sodium chloride (0.5%), ferrous sulfate (0.1%), cupric sulfate (0.005%), nickel sulfate (0.03%), $\beta$-cyclodextrin (2.4%) and FS-anti-foam F20 (antifoaming agent, Dow Corning Co., U.S.A.) (0.2%) was placed and subjected to steam sterilization at 120° C. for 20 min.

To the culture medium, 5 liters of the same seed culture as in Reference Example 1 was transplanted and incubated at 25° C. for 96 hours with the aeration of 1 VVM and stirring at 165 rpm.

To 60 liters of the culture broth thus obtained, were added 20 liters of water and 2 kg of Hyflo-supercel (Johns Manville Products Co., U.S.A.) and the mixture was filtered to give 70 liters of the filtrate.

By HPLC method described in Example 1, the content of lankacidin C was measured. Lankacidin C was confirmed to be contained in a concentration of 4100 $\mu$g per ml of the filtrate. 1 liter each of the filtrate was added to each of three 10 liter glass lined reactors equipped with stirrers which were numbered from 1 to 3.

To the reactor No. 1 was added 1 liter of methyl isobutyl ketone containing 100 mM acetic anhydride, and to the reactor No. 2 was added 1 liter of methyl isobutyl ketone containing 200 mM ethyl acetate, and to the reactor No. 3 was added 1 liter of methyl isobutyl ketone containing 200 mM acetic acid.

The mixtures in the reactor Nos. 1 to 3 were respectively stirred at 37° C. for 60 min. so that acetylation reaction proceeded. 1 ml each of organic layer of the mixture was picked up and subjected to quantitative analysis of lankacidin A by HPLC method described in Example 1

$$\text{The reaction yield} \left( \frac{\text{the amount of lankacidin A formed}}{\text{the initial amount of lankacidin C}} \times 100 \right)$$

was calculated and shown in Table 6.

Furthermore, from each of the reaction mixtures in the reactors Nos. 1 to 3 lankacidin A was separated and purified by the same procedure as in Example 3.

The crop(g) of the obtained lankacidin A was shown in Table 6.

Table 6 clearly shows that when acetic anhydride is used as a acetyl group donor, lankacidin A is obtained in the highest yield (or crop).

TABLE 6

|  | 1 | 2 | 3 |
|---|---|---|---|
| Reaction yield (% weight/weight) | 95.6 | 10.1 | — (below 0.1%) |
| Crop (g) | 3.28 | 0.33 | 0 |

1: Acetic anhydride, 100 mM concentration
2: Ethyl acetate, 200 mM concentration
3: Acetic acid, 200 mM concentration $$\text{Reaction yield:} \frac{\left(\begin{array}{c}\text{the amount of lanckacidin A}\\ \text{formed in 1 liter of the filtrate}\end{array}\right)}{\left(\begin{array}{c}\text{the amount (4.1 g) of lankacidin C}\\ \text{contained in 1 liter of the}\\ \text{filtrate as a starting material}\end{array}\right)} \times 100$$

Crop: The amount of lankacidin A isolated and purified.

EXAMPLE 23

Two of the three test tubes (each 20 ml capacity with ground stopper) were charged with 2 ml each portion of ethyl propionate, and the remaining one with 2 ml methyl isobutyl ketone. To each of these test tubes was added 10 mg of maridomycin (Formula III

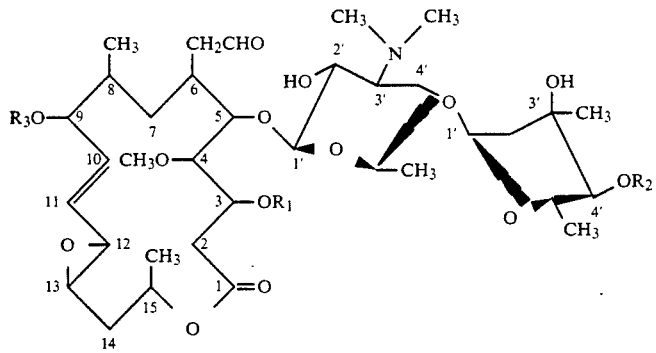

: $R_1=R_2=COCH_2CH_3$, $R_3=H$), followed by stirring well to make a solution.

The two test tubes containing ethyl propionate were respectively named the reaction system (1) and (2), while the test tube containing methyl isobutyl ketone was named the reaction system (3). To these three reaction systems were respectively added 2 ml each of tris (hydroxymethyl)aminomethane-maleate buffer solution (0.2M, pH 7.0) in which was dissolved carboxylesterase obtained in Reference Example 1 at a concentration of 2 mg/ml. To each of the reaction system (2) and (3) was added 20 µl of propionic anhydride, immediately followed by subjecting the stoppered test tubes to shaking at 28° C. for 30 minutes. From the solvent portion of each reaction system was micropipetted 50 µl each solution, which was subjected a thin-layer chromatography (Kieselgel 60, 0.25 mm thick, 20×20 cm, Merck & Co., U.S.A.).

Besides these three test samples corresponding to the reaction system (1), (2) and (3), by using maridomycin III (Formula III: $R_1=R_2=COCH_2CH_3$, $R_3=H$) and 9-propionyl maridomycin III (Formula III: $R_1=R_2=R_3=COCH_2CH_3$), a thin-layer chromatography was carried out employing a solvent system of acetone-toluene (1:1).

By means of color-development with iodine vapor, Rf values of maridomycin III and 9-propionyl maridomycin were confirmed to be 0.46 and 0.57, respectively. The thin layer portions corresponding to maridomycin III and 9-propionyl maridomycin III in the test samples of each reaction system were collected by scratching, which were extracted with a small volume of ethyl acetate. The respective extract solutions were subjected to quantitative determination of the substrate (maridomycin III) and the reaction product (9-propionyl maridomycin III) by means of "Colorimetric Quantitative Determination Method of Maridomycin Antibiotics" described in Agricultural and Biological Chemistry, 43, p. 847 (1979).

The results are as shown by Table 7.

TABLE 7

|  | Substrate (Maridomycin III) | Reaction Product (9-Propinonyl maridomycin III) |
|---|---|---|
| Reaction System (1) | 9.3 | 0.5 |
| Reaction System (2) | trace | 9.9 |
| Reaction System (3) | trace | 9.8 |

(Note)
| Reaction System (1); | Ethyl propionate | 2 ml |
| Reaction System (2); | Ethyl propionate | 2 ml |
|  | Propionic anhydride | 20 µl |
| Reaction System (3); | Methyl isobutyl ketone | 2 ml |
|  | Propionic anhydride | 20 µl |

EXAMPLE 24

A 10 l-capacity galss-linked reaction vessel (with stirrer) was charged with 2 l of methyl isobutyl ketone warmed at 28° C. in advance, in which was dissolved 10 g of maridomycin III. To the solution was then added 2 l of a tris(hydroxymethyl)aminomethane-maleate buffer solution (0.2M. pH 7.0) dissolving 500 mg of carboxyl esterase obtained in Reference Example 1. To the solvent layer was added 20 ml of propionic anhydride, and the reaction was allowed to proceed for one hour under stirring. The reaction solution was shifted to a 10 l capacity separating funnel, and thus the aqueous phase was removed. To the remainder was added 500 ml of an aqueous solution of sodium bicarbonate (2%) (w/v). The mixture was sufficiently stirred, followed by removing the aqueous portion. Washing with an aqueous solution of sodium bicarbonate was repeated once more, followed by washing with 2 l of distilled water twice in the separating funnel. The organic phase was shifted to a 3 l-capacity conical flask, to which was added 100 g of anhydrous sodium sulfate, and the mixture was left standing for two hours. The anhydrous sodium sulfate was filtered off by using filter paper, and the reaction solution was concentrated to dryness to obtain 10 g of 9-propionyl maridomycin III as crude crystals.

The crude crystals were dissolved in 1 l of toluene, and the solution was poured into a column (80 mm diameter, 500 mm length) of silica gel (Merck, U.S.A.) equilibrated with toluene to have the 9-propionyl maridomycin III adsorbed thereon. Three liters of toluene was passed through the column, followed by elution with 2.5 l of a mixture of toluene-acetone (1:0.5) then with a mixture of toluene-acetone (1:1). The eluate was fractionated to 20 ml each portion by using a Tokyo fraction collector (5F-160 type). Identification of the compound was conducted by thin-layer chromatography for identifying propionyl maridomycin III described in Example 23. Fractions containing the object compound were combined and concentrated under reduced pressure to afford 9.1 g of white crystals. Elemental analysis of the crystals; C:H:N=59.7:8.0:1.6, $[\alpha]_D=61.3°$ (c=1, CHCl$_3$). These analytical values are in agreement with those described in Antimicrobial Agents and Chemotherapy, 4, p. 142 (1973). IR spectrum was also in agreement with that described in Chemotherapy, 21, p. 908 (1973).

These crystals are readily soluble in methanol, ethanol and acetone, relatively soluble in chloroform and hardly soluble in water.

When a solution of 5 mg of the crystals in 2 ml of acetone was shaken with 2 ml of hydrochloric acid, reddish-purple color was developed. The solution was shaken with further 2 ml of chloroform, followed by being left standing, then a slightly purple color was developed in the chloroform layer. A mixture of 20 mg of the crystals, 2 mg of thiosemicarbazide and 2 ml of ethanol was heated for 1 hour in a reaction vessel equipped with a reflux condenser on a water bath. After cooling, 0.2 ml of the reaction mixture was taken, to which was added 50 ml of ethanol. Absorption spectrum of thus mixed solution was measured and the maximum absorption was observed at the wavelength of 270-273 nm. The foregoing properties of the crystals as well as the results of confirmatory tests thereof were in agreement with the description of (propionic acid maridomycin) on p. 457 of "Explanation of Minimum Requirements of Antibiotics, Japan" (1986, Yakugyojihosha).

What is claimed is:

1. A process for producing a carboxylic acid ester which comprises reacting an hydroxy group containing compound, wherein the hydroxy group being reacted is either a primary or secondary hydroxy group, with a carboxylic anhydride in the presence of carboxylesterase as a catalyst in an organic solvent.

2. The process as claimed in claim 1, wherein the carboxylic anhydride has the molecular weight below 350 and can dissolve in the organic solvent.

3. The process as claimed in claim 2, wherein the carboxylic anhydride is a compound of the formula:

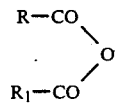

wherein R and R$_1$ respectively is hydrogen, an alkyl, alkenyl, alkynyl, aryl or aralkyl group.

4. The process as claimed in claim 3, wherein R and R$_1$ are the same.

5. The process as claimed in claim 4, wherein R and R$_1$ are a straight-chain or branched alkyl of 1 to 5 carbon atoms or phenyl.

6. The process as claimed in claim 1, wherein the hydroxy compound is an organic compound containing 1 to 10 hydroxy groups which has the molecular weight below 1,500 and which can dissolve in the organic solvent.

7. The process as claimed in claim 6, wherein the hydroxy compound is an organic compound of the formula: R$_2$OH wherein R$_2$ is an alkyl, alkenyl, alkynyl, aryl, aralkyl or heterocyclic group which may be substituted.

8. The process as claimed in claim 1, wherein the hydroxy compound is lower (C$_{2-4}$) alcohols, lankacidin C or maridomycin.

9. The process as claimed in claim 1, wherein the carboxylesterase is organic solvent-soluble carboxyl esterase which is modified with a polyethylene glycol derivative.

10. The process as claimed in claim 9, wherein the organic solvent-soluble carboxylesterase is one which is modified with 2,4-bis(O-methoxypolyethylene glycol)-6-chloro-s-triazine.

11. The process as claimed in claim 1, wherein the carboxylesterase is in the form of the culture filtrate of a carboxylesterase-producing microorganism.

12. The process as claimed in claim 1, wherein the organic solvent can form a two phase system with water.

13. The process as claimed in claim 12, wherein the organic solvent is a ketone or an ester.

14. The process as claimed in claim 1, wherein the organic solvent is methyl ethyl ketone, methyl n-propyl ketone, methyl n-butyl ketone, methyl isobutyl ketone, methyl acetate or ethyl acetate.

15. The process as claimed in claim 1, wherein the reaction is conducted at a temperature in the range of 5° to 90° C. and the pH value in the range of from 2 to 10.

16. The process as claimed in claim 7, wherein the hydroxy compound is an alcohol, phenol, 8-quinolinol, hydroxypiperidine, antibiotic, fibrostatin E or fibrostatin F.

17. A process for producing lankacidin A which comprises reacting lankacidin C with acetic anhydride in the presence of carboxylesterase as a catalyst, said carboxyl esterase being in the form of a culture filtrate of Streptomyces rochei var. volubilis, in methyl isobutyl ketone.

18. A process for producing a carboxylic acid ester which comprises reacting a lankacidin antibiotic having a hydroxy group at the 14-position or a maridomycin antibiotic having a hydroxy group at the 9-position with a carboxylic anhydride to esterify said hydroxy group in the presence of carboxylesterase originating from Streptomyces rochei var. volubilis.

19. A process for producing a carboxylic acid ester which comprises reacting a primary or secondary C$_{2-4}$ alcohol, a lankacidin antibiotic having a hydroxy group at the 14-position or a maridomycin antibiotic having a hydroxy at the 9-position, with a carboxylic anhydride to esterify said hydroxy group, in the presence of carboxylesterase originating from Streptomyces rochei var. volubilis, in an organic solvent.

* * * * *